(12) United States Patent
Florent et al.

(10) Patent No.: US 9,095,308 B2
(45) Date of Patent: Aug. 4, 2015

(54) VASCULAR ROADMAPPING

(75) Inventors: Raoul Florent, Ville D'Avray (FR);
Pierre Lelong, Nogent sur Marne (FR)

(73) Assignee: Koninklijke Philips N.V., Eindhoven (NL)

( * ) Notice: Subject to any disclaimer, the term of this patent is extended or adjusted under 35 U.S.C. 154(b) by 137 days.

(21) Appl. No.: 13/498,162

(22) PCT Filed: Sep. 17, 2010

(86) PCT No.: PCT/IB2010/054208
§ 371 (c)(1),
(2), (4) Date: Mar. 26, 2012

(87) PCT Pub. No.: WO2011/039673
PCT Pub. Date: Apr. 7, 2011

(65) Prior Publication Data
US 2012/0183189 A1    Jul. 19, 2012

(30) Foreign Application Priority Data
Sep. 29, 2009 (EP) .................................. 09305914

(51) Int. Cl.
| G06K 9/00 | (2006.01) |
| G06K 9/40 | (2006.01) |
| A61B 5/05 | (2006.01) |
| A61B 6/00 | (2006.01) |
| A61B 6/02 | (2006.01) |
| A61B 6/12 | (2006.01) |

(Continued)

(52) U.S. Cl.
CPC . *A61B 6/503* (2013.01); *A61B 6/02* (2013.01);
*A61B 6/12* (2013.01); *A61B 6/481* (2013.01);
*A61B 6/486* (2013.01); *A61B 6/488* (2013.01);
*A61B 6/504* (2013.01); *A61B 6/5235* (2013.01); *G06T 5/50* (2013.01); *G06T 7/0012* (2013.01); *G06T 2207/10081* (2013.01); *G06T 2207/10121* (2013.01); *G06T 2207/20144* (2013.01); *G06T 2207/30021* (2013.01); *G06T 2207/30101* (2013.01)

(58) Field of Classification Search
USPC .......................... 382/131, 132, 274; 600/424
See application file for complete search history.

(56) References Cited

U.S. PATENT DOCUMENTS 7,609,814 B2 * 10/2009 Baumgart .................. 378/98.12
8,554,308 B2 * 10/2013 Florent et al. ................. 600/427
(Continued)

FOREIGN PATENT DOCUMENTS

JP    2006501922 A    1/2006
JP    2007502646 A    2/2007
(Continued)

*Primary Examiner* — Anand Bhatnagar
*Assistant Examiner* — Soo Park

(57) ABSTRACT

Cardiac roadmapping consists in correctly overlaying a vessel map sequence derived from an angiogram acquisition onto a fluoroscopy sequence used during PTCA intervention. This enhanced fluoroscopy sequence however suffers from several drawbacks such as breathing motion, high noise level, and most of all suboptimal contrast-enhanced mask due to segmentation defaults. This invention proposes to reverse the process and to locally overlay the intervention device as seen in fluoroscopy onto an optimal contrast-enhanced image of a corresponding cycle. This drastically reduces or suppresses the breathing motion, it provides the high image quality standard of angiograms, and avoids segmentation defaults. This proposal could lead to a brand new navigation practice in PCI procedures.

20 Claims, 5 Drawing Sheets

(51) Int. Cl.
*G06T 5/50* (2006.01)
*G06T 7/00* (2006.01)

(56) References Cited

U.S. PATENT DOCUMENTS

| | | |
|---|---|---|
| 2006/0120581 A1 | 6/2006 | Eck et al. |
| 2006/0257006 A1* | 11/2006 | Bredno et al. ............... 382/128 |
| 2006/0262966 A1 | 11/2006 | Eck et al. |
| 2007/0038081 A1* | 2/2007 | Eck et al. ..................... 600/437 |
| 2007/0276216 A1 | 11/2007 | Beyar et al. |
| 2008/0064974 A1* | 3/2008 | Boese et al. ................. 600/523 |
| 2008/0267490 A1 | 10/2008 | Gorges et al. |
| 2009/0022262 A1* | 1/2009 | Ohishi ............................. 378/4 |
| 2009/0192385 A1* | 7/2009 | Meissner et al. ............. 600/426 |
| 2010/0049034 A1* | 2/2010 | Eck et al. ..................... 600/424 |
| 2010/0208973 A1* | 8/2010 | Lienard et al. ............... 382/132 |

FOREIGN PATENT DOCUMENTS

| | | |
|---|---|---|
| JP | 2008272470 A | 11/2008 |
| WO | WO2004034329 | 4/2004 |
| WO | WO2005020148 | 3/2005 |
| WO | WO2008104921 | 9/2008 |
| WO | WO2009022288 | 2/2009 |
| WO | WO2008107814 | 9/2009 |

\* cited by examiner

VASCULAR ROADMAPPING

FIELD OF THE INVENTION

The present invention relates to method of and device for vascular roadmapping. Especially, the invention relates to a method for visualizing an instrument in an anatomy part. Furthermore, the invention relates to a corresponding system and a computer program.

BACKGROUND OF THE INVENTION

After a catheter is inserted into the vascular system at an access site, it is advanced along large vessels to the vascular structure that requires treatment. Contrast agent is injected via the catheter and cathlab x-ray equipment records an angiographic sequence that shows the vessels when filled with contrast agent. The diagnostic angiogram acquisitions can be repeated with varying imager geometries. Diagnosis and intervention planning are based on such diagnostic angiograms.

During intervention, a flexible, partially or fully radio-opaque guidewire is advanced to the affected vascular structures (e.g. stenoses in coronaries, neurovascular aneurisms, or arterio-venous malformations). Fluoroscopic low-dose x-ray surveillance visualizes the guidewire and allows for the hand-eye-coordination of the interventionalist while advancing the guidewire. When positioned, the guidewire serves as rail to deliver interventional devices (e.g. balloons for dilation and stent delivery, detachable coils for aneurysm clotting). The delivery and deployment of the interventional devices is also fluoroscopy-controlled.

An overlay technique of the angiogram into the live images (referred to as roadmapping) may be utilized. In such procedures, the vessel structure itself is not visible during the intervention as it is not radio-opaque. Consequently, the navigation and precise positioning of guidewire and interventional devices is tedious, time-consuming, and requires additional contrast agent bursts to clarify the position of the devices relative to the relevant vessels. Due to scatter, both patient and medical staff are exposed to x-ray during the acquisition of diagnostic angiograms and interventional fluoroscopy. Navigation support is desired to reduce the intervention time and to enhance the positioning accuracy. Routinely, a static diagnostic angiogram acquired with a similar imager geometry is displayed next to the live interventional fluoroscopy. For the navigation of guidewire and devices within the vessels, a subjective visual fusion of the static angiogram and the live fluoroscopy is required. An improved context-rich visualization could give important support in navigation. As an approach, preprocessed angiograms can be overlaid onto the fluoroscopic image stream so that vessels and the interventional devices are synchronously displayed on one screen (cf. for example FIG. 1).

A navigation system can therefore help the cardiologists by providing a cardiac roadmap displayed next or overlaid on the live fluoroscopy pictures. Ideally, this cardiac roadmap represents the vessel network acquired during angiography, with the same cardiac phase than the current live image, and registered with respect to breathing movements and patient motions.

In WO 2004034329 A2, there is described a basic method for realizing cardiac roadmapping, relying on the extraction of the cardiac and respiratory cycles, and on the matching of those cycles between the angiogram images (in filled state) and the live images.

Roadmapping is a very important feature since it provides (hopefully) the accurate localisation of the intervention device with respect to the vessel anatomy (otherwise invisible during most of the PCI (Percutaneous Coronary Intervention) time).

Roadmapping is even more interesting in the case of cardiac interventions since the mental registration otherwise performed by the cardiologist between the angiogram (usually one selected image) and the dynamic fluoroscopy sequence is a tiring and inaccurate process.

However, the enhanced fluoroscopy sequence that contains the roadmapping mask that comes from the angiogram sequence suffers from several serious drawbacks.

It is quite impossible to overlay the full angiogram to the fluoroscopy image because this creates background mixings and all sorts of disagreeable visual effects. As a consequence, in practice, the cardiac roadmap is deduced from the angiogram through a segmentation process that extracts a mask which is assumed to be a good segmentation of the injected coronaries. Unfortunately, such a segmentation process is complex and often (if not always) produces a mask which is highly suboptimal (incomplete vessels or over segmentations, artefacts, temporal instability).

The other drawbacks are relative to fluoroscopy. The navigation image (a real-time fluoroscopy sequence) is very noisy, and it contains possibly strong breathing motion.

SUMMARY OF THE INVENTION

The present invention proposes to locally overlay the intervention device as seen in the fluoroscopy sequence onto a selected contrast-enhanced image of a corresponding cycle, instead of overlaying a mask segmented in the contrast-enhanced image onto the fluoroscopy images.

It is an object of the invention to provide a method and device eliminating or at least reducing the above mentioned drawbacks.

It is a further object of the invention to provide for a better visualization of an instrument in an anatomy part.

This is achieved by the subject matter of each of the respective independent claims. Further embodiments are described in the respective dependent claims.

In general, it is achieved by a method for visualizing an instrument in an anatomy part, comprising the steps of receiving a contrast-enhanced image of the anatomy part, receiving a fluoroscopy image including the instrument in the anatomy part, defining an area of the fluoroscopy image in which area at least a portion of the instrument is included, and combining the fluoroscopy image of the defined area with the contrast-enhanced image.

It is noted that an anatomy part into which an instrument may be introduced, may be a blood vessel, a cardiac chamber or an aneurysm.

Because the images used for navigation purposes, may now be contrast-enhanced images like angiograms or atriograms or ventriculograms, the image quality at navigation time becomes that of contrast-enhanced imaging time, that may be much better than the fluoroscopy image quality.

Because only the best filled e.g. angiogram cardiac cycle may be selected for this process, the breathing motion may be now reduced to a single cardiac cycle. If breath-hold (even relative) is requested from the patient, the breathing motion during about 1 second (=1 cardiac cycle) may virtually be reduced to zero.

Because no segmentation of the vessels in e.g. the angiogram is required, since only the area next to the device, as seen in fluoroscopy, is overlaid to the angiogram that natively contains the vessels in an optimal injection state, no segmentation defaults may impair the final result.

According to another embodiment, the method may further comprise a step of detecting at least a portion of the instrument in the fluoroscopy image, wherein the portion of the instrument may be a tip portion of the instrument.

Therefore, instead of navigating within the fluoroscopy world, possibly but imperfectly enhanced by a vessel mask, the navigation could occur within the angiogram world, virtually free of noise and of breathing motion, and with an optimal view of the vessels, but with the additional local overlay of the intervention device (namely, the wire tip).

It is noted that a portion of interest of an instrument may be detected in a fluoroscopy image manually or by means of automatic procedures utilizing appropriate image processing computer software. Based on such detection, also the area surrounding the portion of the instrument may be defined manually by for example input, or may be defined automatically according to a previously determined procedure or software algorithms. It will be understood that a definition of an area may be performed automatically after a portion of an instrument is detected manually, or the area may be defined manually after the system has detected aspects in a fluoroscopy image including an instrument, and supposed a portion by for example high-lighting the same.

According to another embodiment, a plurality of contrast-enhanced images is received, wherein a cyclic motion of the structures in the contrast-enhanced images is identified, a plurality of fluoroscopy images is received, wherein a cyclic motion of the structures in the fluoroscopy images is identified, and a selected fluoroscopy image of the identified area is combined with a contrast-enhanced image of a corresponding motion cycle.

This may provide for the advantage that a suitable contrast-enhanced image out of a sequence of images may be easily selected which may have the corresponding motion cycle as a current live fluoroscopy image.

The result of the method, i.e. the achieved combined images, may be displayed on a suitable device, for example on a monitor.

The method according to the invention may be used advantageously by an imaging system for PCI (Percutaneous Coronary Intervention) in catheter laboratories, to treat cardiac stenoses.

According to another aspect of the invention, a system for vascular roadmapping is provided, comprising a device for generating a contrast-enhanced image, a device for generating a fluoroscopy image, a processing device for processing the fluoroscopy image and for combining the processed fluoroscopy image with the contrast-enhanced image.

The processing device of the system may be adapted to detect a portion of an instrument in the fluoroscopy image and may further be adapted to define an area of the fluoroscopy image which area includes the detected portion of the instrument.

It is noted that the instrument might be, on the one hand, a flexible or stiff catheter or wire tip or an electrode, and on the other hand also a biopsy device, a cannula or trocar. It can also be an endoprothesis such as a stent, an occluder (e.g. a Patent Foramen Oval occluder), an artificial valve, etc . . .

Furthermore, the processing device may be adapted to combine a fluoroscopy image of the defined area with a contrast-enhanced image.

According to another embodiment, the processing device of the system is adapted to identify a cyclic motion in a series of contrast-enhanced images and is adapted to identify a cyclic motion in a series of fluoroscopy images, wherein the processing device is further adapted to combine a selected processed fluoroscopy image with a contrast-enhanced image of a corresponding motion cycle. This can be achieved by a purely image-based method, or through the use of external non-imaging systems such as ECG (electro cardiogram) signal.

The system may further comprise a monitor for displaying the combined images.

According to a further aspect of the invention, a computer program for vascular roadmapping is provided which, when executed on a processing device of the system according to the invention, causing the system to perform the method according to invention. Therefore, the method according to the invention may be performed substantially automatically, or at least predominantly automatically. Therefore, the computer program may comprise sets of instructions for gathering and at least temporarily storing at least one contrast-enhanced image generated by an appropriate system, sets of instructions for gathering and at least temporarily storing at least one live fluoroscopy image also generated by an appropriate system, sets of instructions for identifying a portion of an instrument shown in the fluoroscopy image, and sets of instructions for combining at least an area of the fluoroscopy image with the contrast-enhanced image.

Further, the computer program may comprise sets of instructions for loading data from a data base including previously recorded image information, or may comprise sets of instructions for information retrieval from a user.

Such a computer program is preferably loaded into a work memory of a data processor. The data processor is thus equipped to carry out the method of the invention. Further, the invention relates to a computer readable medium, such as a CD-ROM, at which the computer program may be stored. However, the computer program may also be presented over a network like the World Wide Web and can be downloaded into the work memory of a data processor from such a network.

It has to be noted that embodiments of the invention are described with reference to different subject matters. In particular, some embodiments are described with reference to method type claims whereas other embodiments are described with reference to apparatus type claims. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can also be derived from the examples of the embodiments to be described herein after and are explained with reference to examples of embodiments also shown in the figures, but to which the invention is not limited.

DETAILED DESCRIPTION OF EMBODIMENTS

Figure 1:
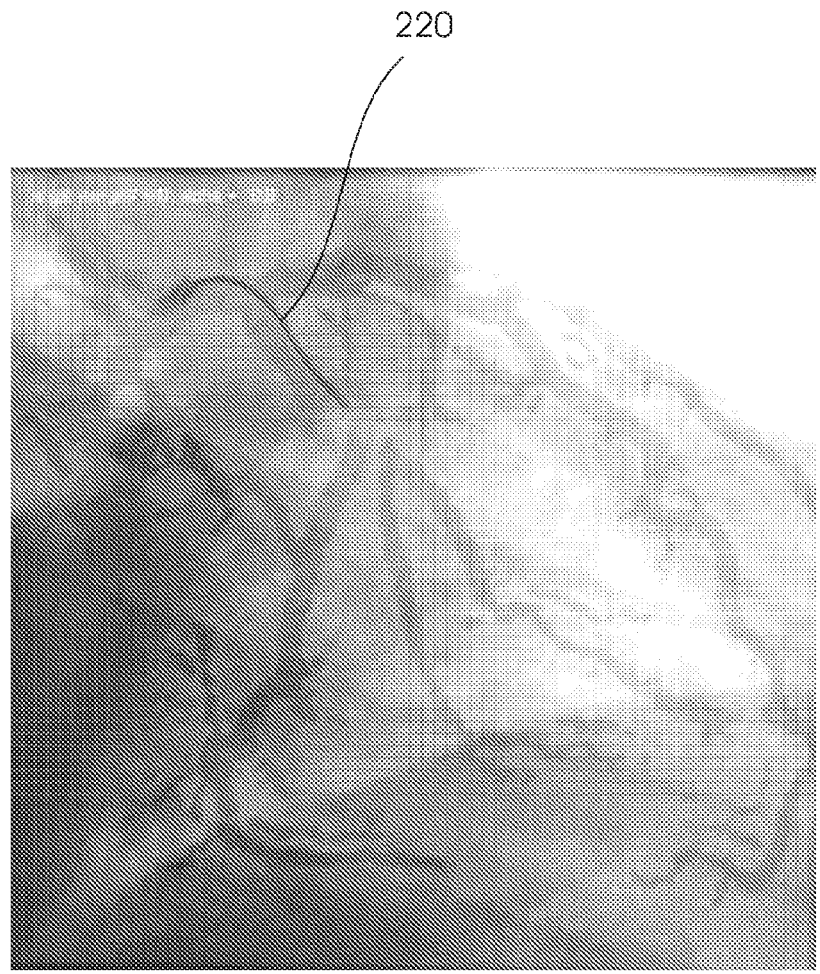
FIG. 1 shows an image provided by a method according to prior art.

FIG. 1 shows a typical result obtained with a classical cardiac roadmapping technique, wherein a previously recorded angiography image is laid over a live fluoroscopy image including a portion 220 of an instrument.

Figure 2:
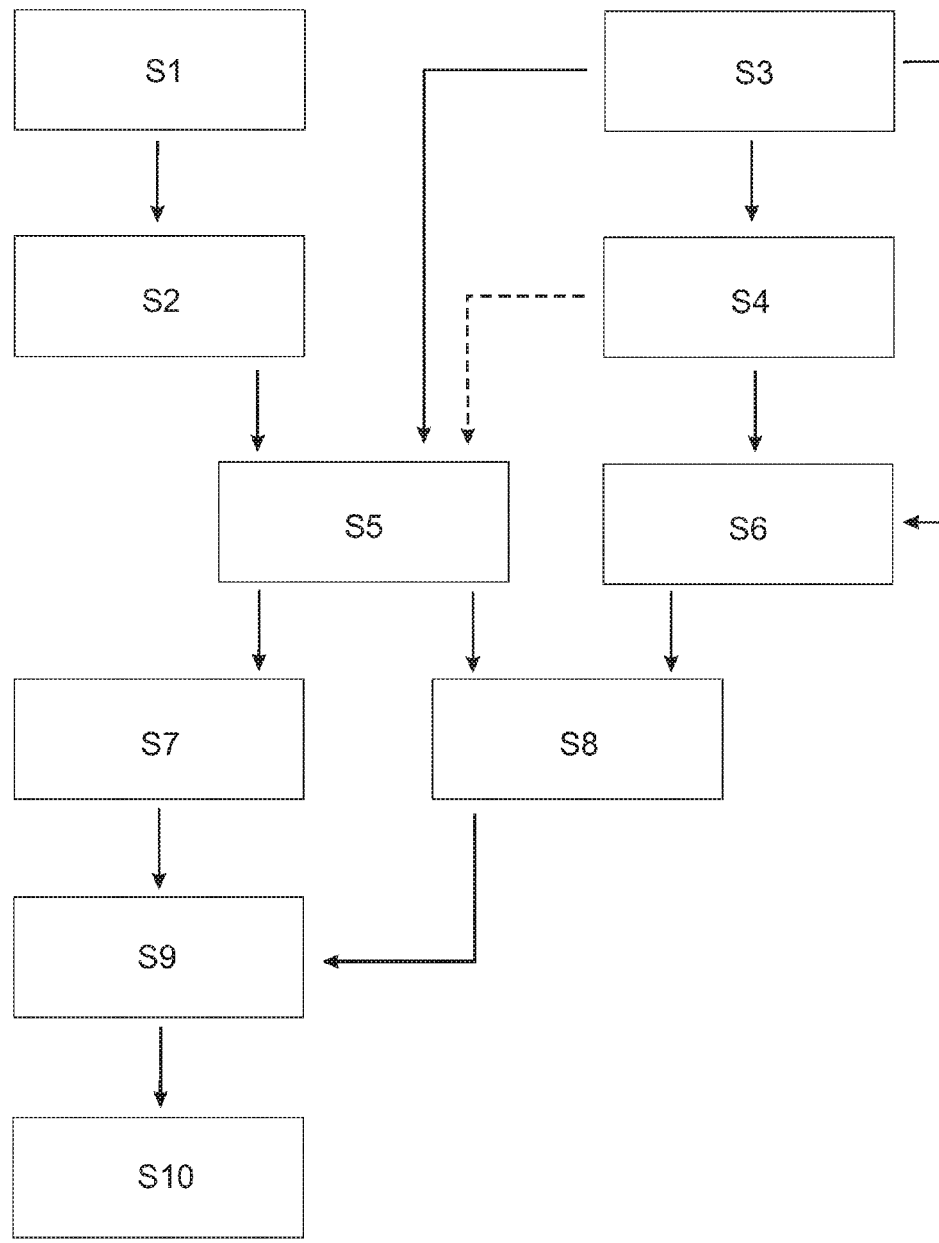
FIG. 2 shows flowchart of a method according to the invention.

The flowchart in FIG. 2 illustrates the principle of the vascular roadmapping according to the invention, comprising the following steps. It will be understood that the steps described with respect to the method are major steps, wherein these major steps might be differentiated or divided into several sub steps. Furthermore, there might be also sub steps between these major steps. Therefore, a sub step is only mentioned if that step is important for the understanding of the principles of the method according to the invention.

In step S1, an angiography image or a plurality of images is generated. As previously mentioned, the image or images generated in step S1 may also be contrast-enhanced images like atriograms or ventriculograms.

In step S2 (following step S1), using either image processing based methods or also involving ECG signals, applied on the considered angiogram sequence, an identification of the angiography frames constituting a full cardiac cycle in an optimally Contrast Agent (CA) injected state is achieved. Usual motion compensation and correlation techniques can typically be involved at this stage.

In step S3, at least one fluoroscopy image is generated. Usually, a series of live fluoroscopy images is generated.

In step S4 (following step S3), an instrument detection is applied on the current fluoroscopy image (in real-time). It aims at detecting the intervention tool (typically the wire tip). Image processing techniques using ridge filters and temporal tracking are typical approaches to be used for such a task. The output of this step is simply the localisation of the instrument, or of some of the instrument's points (such as the very tip of a wire), or a portion of the instrument. This can also be a stent marker or a couple of markers, etc.

In step S5 (utilizing the data of steps S2, S3 and possibly S4), using ECG signals and/or image processing techniques it is possible to determine, to which of the selected angiography images the current fluoroscopy image having the same cardiac cycle, corresponds, and through which geometrical transform (typically a translation suffices to compensate for breathing motion). It is also possible to use the output of the device detection step to help achieving this registration task (since the device in the fluoroscopy image is likely to pertain to a filled vessel in the corresponding angiography image). The output of this step is the angiography frame index, and the matching geometrical transform parameters.

In step S6 (following step S4 and utilizing data of step S3), an instrument mask is created. From the instrument localisation achieved in step S4, it is simple to create a mask containing the instrument or at least a portion of the instrument. A simple over-segmentation is sufficient at this step. Ridge filters, region growing, morphology techniques can be applied for this task. The output is an instrument mask that can be dilated so as to clearly contain the targeted tool, even if it entails over-segmentation. The mask surrounds an area of the fluoroscopy image which includes the instrument.

In step S7 (following step S5), the angiography frame that corresponds best to the current fluoroscopy image (same cardiac cycle) found at step S5, is simply selected from the extracted motion cycle in the angiography images.

In step S8 (based on step S5 and S6), the instrument mask created in step S6, can then be simply registered through the application of the geometrical transform computed in the previous step.

In step S9 (based on steps S7 and S8), the selected angiography frame is mixed or combined with the registered instrument mask. This simply amounts in blending the grey levels of both sources, with possible transparency values to remove some unlikely pixels from the mask. In other words, only the area or part of the fluoroscopy image, which is inside the mask and thus is in the direct vicinity of the instrument is combined with the full angiography image, wherein the angiography image provides for an overview and the area of the fluoroscopy image provides for the detail information about the location of the instrument.

In step S10, the result is displayed for example on a monitor. Of course, in such a scheme, steps S4, S6, S8 can be repeatedly applied on several devices present in the image (e.g. several wire tips in complex percutaneous coronary interventions), and all the resulting registered masks (one per detected device) might be combined to the angiogram in step 9.

Figure 3:
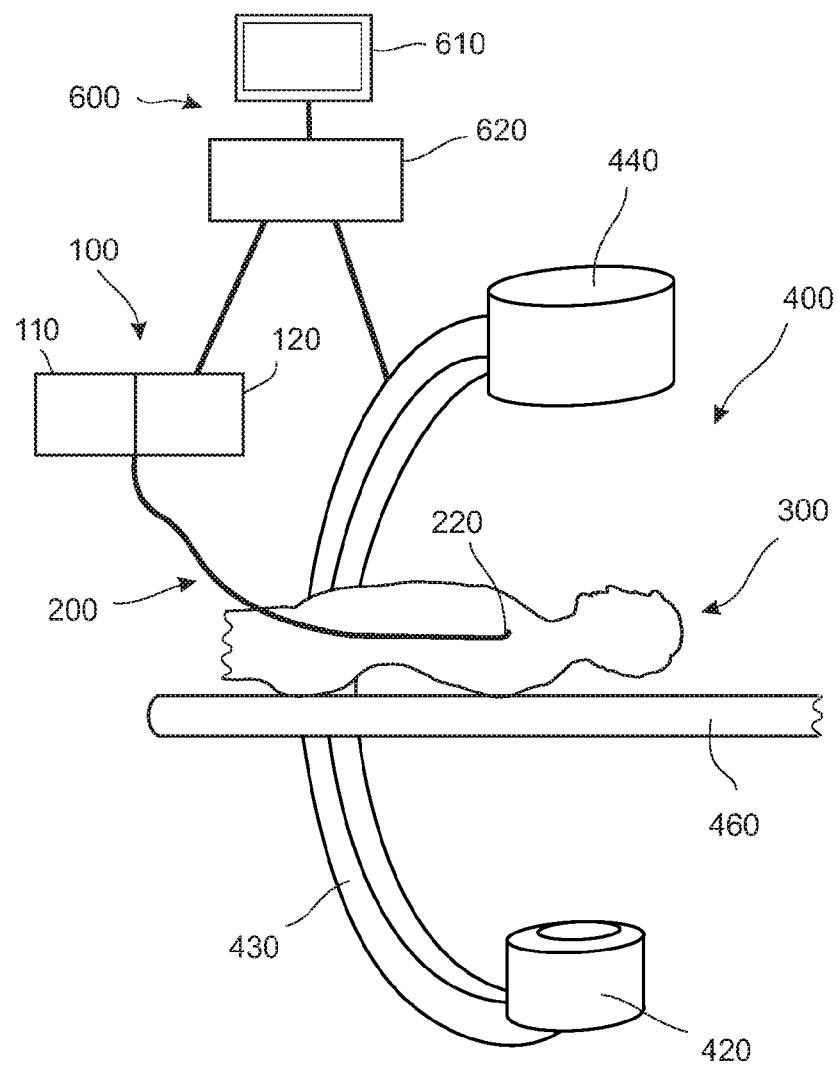
FIG. 3 shows an example of a system according to the invention.

FIG. 3 shows an exemplary system according to the invention, the system including a console 100 for an instrument 200, which instrument may be introduced into a patient 300. Furthermore, an x-ray device 400 is arranged relative to the patient such that a fluoroscopy image of a region may be generated in which the tip portion 220 of the catheter 200 is located. Finally, a processing unit 600 is provided which may control the generating of the fluoroscopy image by means of the x-ray device 400, as well as the console 100 to control functions of the catheter 200, if appropriate.

Here, the controller 100 may include a unit 110 by means of which a contrast agent may be delivered, so that e.g. an angiography image or a series of angiography images may be generated. On the other hand, by way of the unit 110, drugs may be injected. Further, the console 100 may comprise a device 120 by means of which for example the orientation of the tip portion 220 of the catheter 200 may be controlled, or which may control special functions of the catheter like laser application or a placing of a prosthesis like a stent, or introducing and inflating a balloon. It is noted that the console 100 may include also more than two units or devices, depending on the intended treatment.

The x-ray device 400 includes an x-ray source 420 as well as a detector for x-ray radiation 440, wherein both, the x-ray source 420 as well as the x-ray detector 440 are arranged at a C-arm 430 to ensure a proper orientation of both, relative to each other. The patient 300 may be positioned at a table 460.

The processing unit 600 includes first of all a control unit 620 and further a monitor 610, wherein an output of information with respect to the current location of for example a tip of an instrument may be shown on said monitor.

The processing unit 600 may further comprise a processing device or working memory on which a computer program, to perform the vascular roadmapping according to the invention, may be stored and/or executed.

Figure 4:
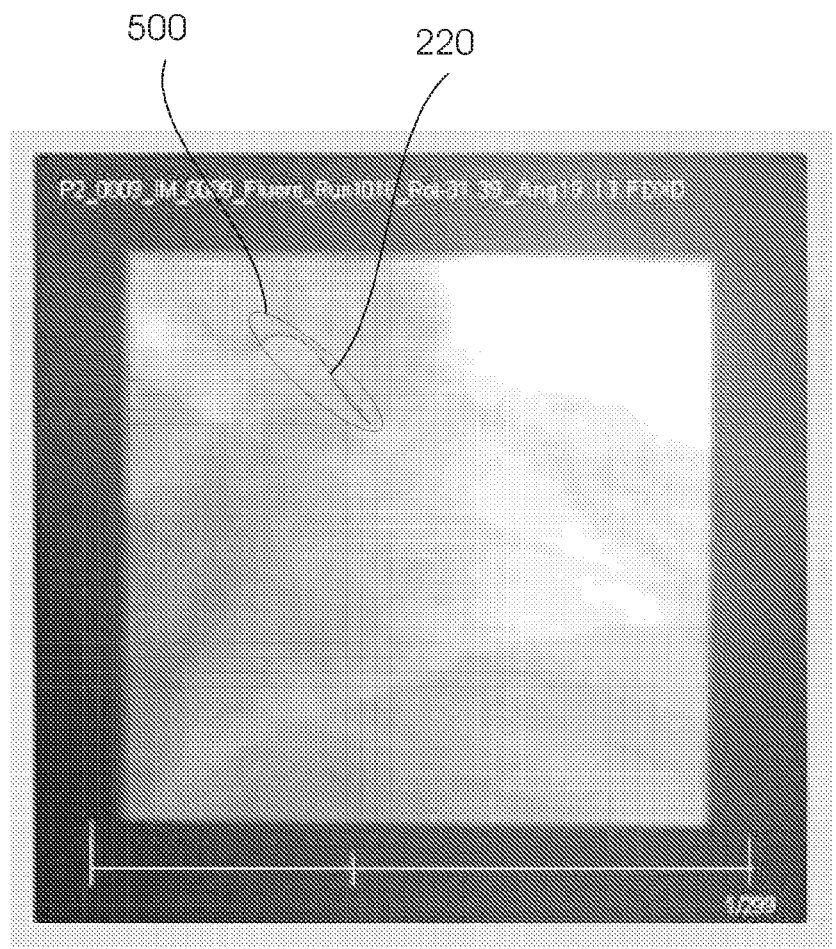
FIG. 4 shows an example of a fluoroscopy image.

FIG. 4 shows an example of a fluoroscopy image as generated in step S3 of the above described method. In step S4, the portion 220 of an instrument may be detected, wherein in step S6, a mask 500 is created which surrounds the detected portion 220. It is noted that the mask may have any other form as the exemplary oval form depict in FIG. 4. The mask may be also circular or rectangular, or may have the form of the detected portion 220 but being enlarged so that the portion 220 of the instrument together with the surrounding area in the vicinity of the portion is placed inside the mask.

Figure 5:
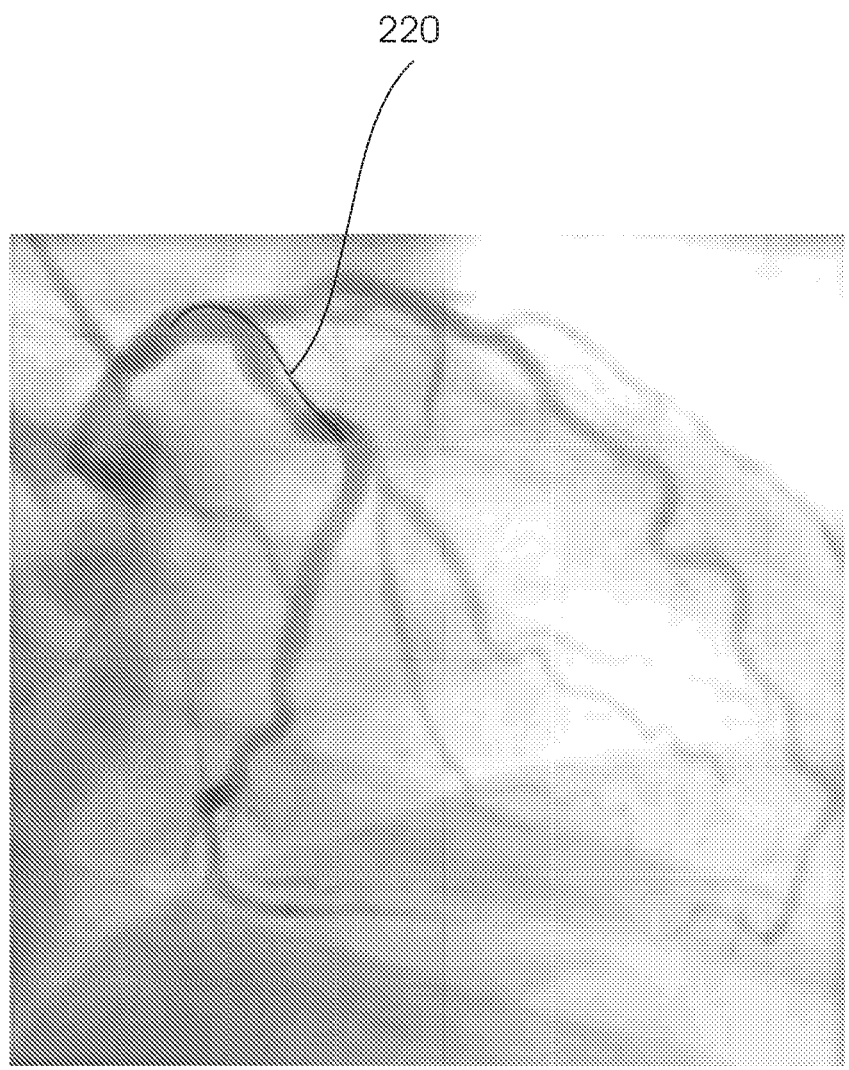
FIG. 5 shows an image provided by the method according to the invention.

FIG. 5 shows actual results produced by vascular roadmapping according to the invention. In other words, FIG. 5 shows an angiography image into which only the area identified by the mask 500 is introduced as an overlay. In comparison with FIG. 1, one can clearly see the visibility gain one can expect from such a technique. What the figures do not show is the breathing motion cancelling permitted by the vascular roadmapping technique.

While the invention has been illustrated and described in detail in the drawings and afore-going description, such illustrations and descriptions are to be considered illustrative or exemplary and not restrictive, the invention is not limited to the disclosed embodiments.

Other variations to the disclosed embodiments can be understood and effected by those skilled in the art in practicing the claimed invention, from a study of the drawings, the disclosure and the appended claims. In the claims, the word 'comprising' does not exclude other elements or steps, and the indefinite article 'a' or 'an' does not exclude a plurality. A single processor or other unit may fulfill the functions of several items recited in the claims.

The mere fact that certain measures are recited and mutually different dependent claims does not indicate that a combination of these measured cannot be used to advantage. A computer program may be stored/distributed on a suitable medium such as an optical storage medium or a solid-state medium supplied together with or as a part of another hardware, but may also be distributed in other forms, such as via the internet or other wired or wireless telecommunication systems. Any reference signs in the claims should not be construed as limiting the scope.

LIST OF REFERENCE SIGNS 100 console
110 unit
120 device
200 instrument
220 tip portion of instrument
300 patient
400 x-ray device
420 x-ray source
430 C-arm
440 x-ray detector
460 table
500 mask
600 processing unit
610 monitor
620 control device

The invention claimed is:

1. A vascular roadmapping apparatus for visualizing an image of an instrument, said image including an anatomy part in which said instrument is disposed, said apparatus comprising a vascular roadmapping processor configured for:
receiving a contrast-enhanced image of said anatomy part, without said contrast-enhanced image having been subjected to blood vessel segmentation that operates, on a contrast-enhanced image in preparation for roadmapping, by deducing a cardiac roadmap although retaining less than a full angiogram;
receiving a fluoroscopy image that includes depiction of, in said anatomy part, said instrument;
defining an area of said fluoroscopy image in which area at least a portion of said instrument, and a region that surrounds said portion but excludes the instrument itself, are included; and,
combining the defined area of said fluoroscopy image with the received contrast-enhanced image, without prior performance of said segmentation on the received contrast-enhanced image, said combining overlaying said area onto said received contrast-enhanced image.

2. The apparatus of claim 1, said processor being further configured for:
receiving a plurality of contrast-enhanced images that are angiography images, said pluratily including said received contrast-enhanced image;
identifying a cyclic motion of structures in said angiography images;
receiving a plurality of fluoroscopy images among which is said fluoroscopy image;
identifying a cyclic motion of structures in said fluoroscopy images; and
combining respectively, in accordance with said identifying a defined area of a fluoroscopy image with a contrast-enhanced image of a corresponding motion cycle, and so as to overlay the depiction of said instrument onto said contrastenhanced image of said corresponding motion cycle.

3. The apparatus of claim 1, said defining comprising detecting, in said fluoroscopy image, said portion of said instrument, said defined area including the detected portion, 4. The apparatus of claim 3, said processor being further configured for defining a mask to thereby spatially delimit part of said fluoroscopy images, said mask including said portion, said mask extending beyond said portion to also include, as the surrounding region, an area of said fluoroscopy image surrounding said portion, said combining comprising combining, with the contrast-enhanced image, said part inside, and delimited by, said mask.

5. the apparatus of claim 3, further configured for said detecting so as to specifically detect said portion, said defined area further including a portion surrounding said detected portion.

6. The apparatus of claim 1, further comprising, as said display, a monitor for displaying said combined image.

7. The apparatus of claim 1, further comprising an x-ray device, said processor being further configured for operating said x-ray device to generate said contrast-enhanced image and to generate said fluoroscopy image.

8. The apparatus of claim 1, said combining comprising combining a contrast-enhanced image that is an angiogram that natively contains blood vesseis in an optimal injection state.

9. The apparatus of claim 1, said receiving of said contrast-enhanced image comprising using x-rays, and x-ray contrast agent, to acquire said contrast-enhanced image.

10. The apparatus of claim 1, furnther configured for detecting, in said fluoroscopy image, at least a portion of said instrument.

11. The apparatus of claim 10, said portion of said instrument being a tip portion of said instrument.

12. The apparatus of claim 1, said preparation being for cardiac roadmapping.

13. A non-transitory computer readable medium embodying a program for visualizing an image of an instrument, said image including an anatomy part in which said instrument is disposed, said program having instruction executable by a processor for performing a plurality of acts, among said plurality there being the acts of:
receiving a contrast-enhanced image of said anatomy part, said contrast-enhanced image not having been subjected to blood vessel segmentation that operates, on a contrast-enhanced image in preparation for roadmapping, by deducing a cardiac roadmap although retaining less than a full angiogram;

receiving a fluoroscopy image that includes depiction of, in said anatomy part, said instrument;

defining an area of said fluoroscopy image in which area at least a portion of said instrument, and a region that surrounds said portion but excludes the instrument itself, are included; and combining, without prior performance of said segmentation on the received contrast-enhanced image, the defined area of said fluoroscopy image with the received contrast-enhanced image, said combining overlaying said area onto said received contrast-enhanced image.

14. The computer readable medium of claim 13, said combining comprising combining a contrast-enhanced image that is an angiogram that natively contains blood vessels in an optimal injection state, 15. The computer readable medium of claim 13, said receiving of said contrast-enhanced image comprising using x-rays, and xray contrast agent, to acquire said contrast-enhanced image.

16. The computer readable medium of claim 13, said paraiion being for cardiac roadmapping.

17. An apparatus for vascular roadmapping, comprising:
a vascular roadmapping processor configured for:
receiving a contrast-enhanced image of said anatomy part, without said contrast-enhanced image having been subjected to blood vessel segmentation that operates, on a contrast-enhanced image in preparation for roadmapping, by deducing a cardiac roadmap although retaining less than a full angiogram;

detecting a portion of an instrument in a fluoroscopy image;

defining a mask to thereby spatially delimit part of said fluoroscopy image, said mask including said portion, said mask extending beyond said portion to also include an area of said fluoroscopy image that surrounds said portion but excludes the instrument itself; and combining, with the contrast-enhanced image, said part inside, and delimited by, said mask.

18. The apparatus of claim 17, configured for identifying a cyclic motion in a series of contrast-enhanced images and identifying a cyclic motion in a series of fluoroscopy images, said combining comprising selecting, from among said fluoroscopy images. said part kw combination with a contrast-enhanced image of corresponding motion cycle.

19. The apparatus at claim 17, further comprising a monitor and further configured for, via said monitor, displaying the combined image.

20. The apparatus of claim 17, said fluoroscopy image depicting said instrument as within an anatomy part, said combining being without prior performance of said segmentation on the generated contrast-enhanced image, said combining overlaying the depiction of said instrument onto said received contrast-enhanced image.

* * * * *